(12) United States Patent
Belleville et al.

(10) Patent No.: US 8,317,715 B2
(45) Date of Patent: Nov. 27, 2012

(54) ECCENTRIC PRESSURE CATHETER WITH GUIDEWIRE COMPATIBILITY

(75) Inventors: M. Claude Belleville, Quebec (CA); Sébastien Lalancette, St-Augustin de Desmaures (CA); MengChe Looi, Quebec (CA); M. Daniel Nahon, Ottawa (CA); Marwane Berrada, Montreal (CA); Steve Arless, Bale Durle (CA); Olivier Bataille, Kirkland (CA)

(73) Assignee: Opsens Inc., Québec (CA)

( * ) Notice: Subject to any disclaimer, the term of this patent is extended or adjusted under 35 U.S.C. 154(b) by 180 days.

(21) Appl. No.: 12/725,951

(22) Filed: Mar. 17, 2010

(65) Prior Publication Data

US 2010/0241008 A1    Sep. 23, 2010

Related U.S. Application Data

(60) Provisional application No. 61/160,933, filed on Mar. 17, 2009.

(51) Int. Cl.
    *A61B 5/02* (2006.01)

(52) U.S. Cl. .................................. 600/486; 600/485

(58) Field of Classification Search .............. 600/486, 600/585
    See application file for complete search history.

(56) References Cited

U.S. PATENT DOCUMENTS

| | | |
|---|---|---|
| 4,771,782 A | 9/1988 | Millar |
| 4,850,358 A | 7/1989 | Millar |
| 4,966,148 A | 10/1990 | Millar |
| 5,046,497 A | 9/1991 | Millar |
| 5,395,311 A | 3/1995 | Andrews |
| 5,533,957 A | 7/1996 | Aldea |
| 5,597,377 A | 1/1997 | Aldea |
| 6,142,958 A * | 11/2000 | Hammarstrom et al. ..... 600/585 |
| 6,146,354 A | 11/2000 | Beil |
| 6,471,656 B1 * | 10/2002 | Shalman et al. ............. 600/486 |
| 6,852,261 B2 | 2/2005 | Benjamin |

FOREIGN PATENT DOCUMENTS

| | | |
|---|---|---|
| CA | 2734698 | 3/2010 |
| WO | WO 2010-030882 | 3/2010 |

OTHER PUBLICATIONS

PCT—International Search Report (ISR)—PCT/CA2010/000396 (Form PCT/ISA/210)—Jul. 12, 2010—3 pages.

* cited by examiner

*Primary Examiner* — Michael Kahelin
*Assistant Examiner* — Christian Jang
(74) *Attorney, Agent, or Firm* — Benoît & Côté

(57) ABSTRACT

There is herein described a catheter for measuring a pressure in a cardiovascular system. The catheter comprises: a guiding tube adapted for insertion into the cardiovascular system. The guiding tube defines a lumen for sliding a guidewire therethrough. The catheter further comprises a tip pressure sensor eccentrically mounted relative to the guiding tube and a signal communication means extending therefrom. The tip pressure sensor is for sensing a pressure in the cardiovascular system and the signal communicating means is for transmitting a signal indicative of the pressure to a processing device in order to obtain a pressure measurement reading.

33 Claims, 9 Drawing Sheets

ECCENTRIC PRESSURE CATHETER WITH GUIDEWIRE COMPATIBILITY

CROSS-REFERENCE TO RELATED APPLICATIONS

The present application claims priority of U.S. provisional application 61/160,933 filed Mar. 17, 2009 and entitled "ECCENTRIC PRESSURE CATHETER WITH GUIDEWIRE COMPATIBILITY", the content of which is incorporated herein by reference.

Field of Art

The field of this disclosure relates to catheters for use in the cardiovascular system to measure pressure. More specifically, the present disclosure relates to catheter devices having the capability to be used in conjunction, and be compatible, with standard guidewire assemblies.

BACKGROUND

Pressure measurement guidewires have been in existence since at least the last ten years. These guidewires are most commonly used to measure pressures distal to a lesion, most commonly in the coronary vasculature. By calculating the ratio between the measured pressure distal to the lesion and some point more proximal, most commonly in the ascending aorta or the coronary tree root, the fractional flow reserve (FFR) is obtained. The FFR is now commonly used to assess the degree of lesion stenosis and thereby informs the physician as to the most appropriate treatment strategy. Recently there has been greater clinical acceptance of the importance of measuring translesional pressure gradients and calculating FFR prior to deciding whether to place a stent. As detailed in Pijls et al. "Percutaneous Coronary Intervention of Functionally Nonsignificant Stenosis 5-Year Follow-Up of the DEFER Study." J Am Coll Cardiol (2007) vol. 49 (21) pp. 2105-2111, which is hereby incorporated by reference, stenting a vessel with an FFR greater or equal to 0.75 does not lead to better outcomes compared to non stenting. Another recent study detailed in Fearon et al. "Rationale and design of the fractional flow reserve versus angiography for multi-vessel evaluation (FAME) study." American Heart Journal (2007) vol. 154 (4) pp. 632-636, which is also hereby incorporated by reference, a multi-center multi-lesion disease, had a similar conclusion suggesting that not stenting an FFR greater or equal to 0.80 lesion leads to better outcomes. It is expected that FFR will soon become the standard of care to document lesion gradient and determine whether a stent is appropriate.

A common method of measuring the pressure distal to the lesion is through the use of a specialized guidewire with pressure sensors mounted in the guidewire. This is exemplified by the devices described in U.S. Pat. Nos. 6,167,763; 6,112,598 and 6,565,514. These types of devices are now commonly used in coronary vasculature, although their use is not limited to the coronary arteries and they could be used in other vessels of the body. These guidewires serve a double function of pressure measurement to obtain FFR, while at the same time, are used in a fashion similar to standard guidewires, to deliver balloon angioplasty and/or stent therapeutic devices to the diseased plaque location.

Because of this double function, the pressure measuring guidewires necessarily have a more complex construction than standard guidewires used in percutaneous coronary interventions to guide therapeutic devices to the coronary tree. Because of this more complex construction, current guidewires with an embedded pressure sensor have handling and other characteristics which are sub optimal. With the constraints for receiving a pressure sensor such as the use of hollow tubing, the design of a guidewire with adequate handling characteristics leads to limited performances. They have inferior lesion crossing characteristics, are more difficult to place in position and have inferior pushability and torquability characteristics. Physicians accept these inferior handling characteristics as the necessary compromise in order to be able to perform pressure measurements and FFR calculations with the same guidewire used to deliver stent and balloon devices.

Accordingly a need exists for an improved pressure measurement catheter to measure FFR while allowing the physician to use a standard guidewire with optimal handling characteristics.

SUMMARY

To be adaptable to standard off-the-shelf guidewires, the proposed device has a catheter with a pressure sensor eccentrically mounted relative to the longitudinal axis of the guidewire to measure the pressure distal to the lesion. The proposed pressure measuring catheter is designed, in one embodiment, as a 'rapid exchange' catheter. In other embodiments, or additionally, it is designed to function similarly to a monorail, in order to be advanced and guided to a working location using a standard guidewire. By placing the pressure sensor within a catheter and separating the guidewire functions from the pressure measuring functions, a physician can perform FFR while at the same time use his/her preferred guidewire. This solution removes the need to compromise between guidewire performance and the ability to perform FFR. The diameter of the proposed catheter that stands within the lesion while performing FFR is minimal, thereby minimizing additional pressure drop across lesion.

In accordance with an embodiment, there is provided a catheter for measuring a pressure in a cardiovascular system. The catheter comprises: a guiding tube adapted for insertion into the cardiovascular system. The guiding tube defines a lumen for sliding a guidewire therethrough. The catheter further comprises a tip pressure sensor eccentrically mounted relative to the guiding tube and a signal communication means extending therefrom. The tip pressure sensor is for sensing a pressure in the cardiovascular system and the signal communicating means is for transmitting a signal indicative of the pressure to a processing device in order to obtain a pressure measurement reading.

BRIEF DESCRIPTION OF THE DRAWINGS

Further features and advantages of the present invention will become apparent from the following detailed description, taken in combination with the appended drawings which are meant to be exemplary only, in which.

DETAILED DESCRIPTION

The proposed concept is a stand-alone eccentric pressure catheter device which can be universally used with a readily available guidewire. If the pressure sensor is small enough, it is possible to mount the sensor eccentrically relative to the guidewire while keeping the ability to cross a lesion and assess FFR.

Figure 1:
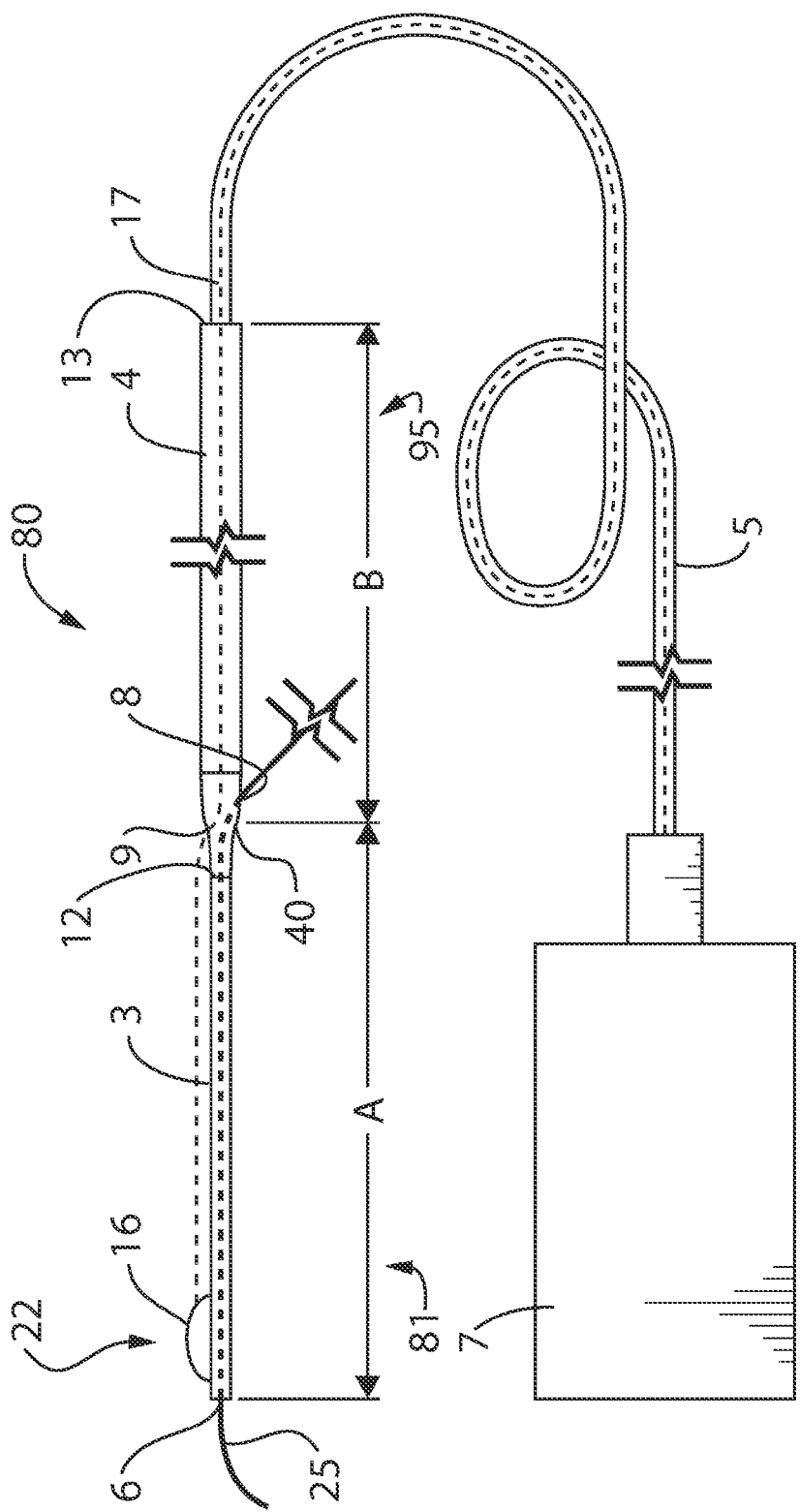
FIG. 1 is a schematic view of a catheter device in accordance with an embodiment.

Referring to FIG. 1, there is shown a first embodiment of a catheter device 80 defining a distal portion 81 for insertion into a cardiovascular system, and a proximal portion 95 extending outside patient body for transmitting mechanical force and relaying pressure measurements information.

A catheter tip assembly 22 is at the distal portion 81 of the catheter device 80. The catheter tip assembly 22 comprises a sensor 16. The pressure sensor 16 is mounted to the side wall or anywhere other than the geometrical centre (i.e. eccentrically) of a guiding tube 3. The catheter tip assembly 22 comprises a pressure sensor 16 and a communication means 17 (e.g., an optical fiber) for communication with a processing device 7.

In this first illustrated embodiment, the guiding tube 3 is a hollow tubing with a lumen extending along at least a portion of its length. The lumen is used for entering a guidewire 25 therethrough. The length of the guiding tube 3 in this case defines a distal section A of the catheter device 80 which is representative of the distal portion 81.

The guiding tube 3 is slid over and guided by a guidewire 25 which enters the lumen (not numbered) of the guiding tube 3. The guidewire 25 then exits the guiding tube 3 from the first opening 8 located at guiding tube proximal end 12 which is in one embodiment, approximately 30 to 40 cm from distal end 6 of the guiding tube 3, illustrated as section A. Section A thus extends from the distal end 6 to a proximal end 12 at first opening 8. The guiding tube 3 has as small a diameter as possible while still delivering a minimum pushability and accommodating the guidewire within the lumen.

In one embodiment, the guiding tube 3 is a relatively soft tubing having a length of about 20 to 30 cm long so as to slide over the guidewire 25.

Still referring to FIG. 1, and by way of a non limiting example, the guiding tube 3 is made of polyimide tubing with an inner diameter (ID) of about 0.016" and outer diameter (OD) of about 0.018". Alternatively, a braided polyimide tubing with an ID of about 0.016" and OD of about 0.021" is used to provide additional pushability and resistance to kinking.

In the embodiment of FIG. 1, section B of the catheter device 80 as shown in FIG. 1, extends from the proximal end 12 at opening 8 of section A. Section B provides the pushability required to push section A at a lesion site and further through it. Section B has a tubing 4 which is made, in one embodiment, of a stainless steel hypo-tube with an outer diameter of about 0.024" and an inner diameter of about 0.016". In one instance, the length of the tubing 4 is of the order of 100 cm. Section B is illustrated in this embodiment as a proximal portion 95 of the device 80.

In an embodiment where the tubing 4 is a hypo-tube, such hypo-tube is spliced to the guiding tube 3 in different ways. In any case, a connecting device 40 that connects in between the guiding tube 3 and the tubing 4 can also be used. The connecting device 40 can also serve to provide an opening 8 for the guidewire 25 to exit the guiding tube 3 distally of the tubing 4, as well as another opening 9 used to enter a signal communication means 17 such as a lead wire or an optical fiber into the tubing 4.

The communication means 17 brings the signal from the tip pressure sensor 16 located on distal end of guiding tube 3 in this example, to a processing device 7 located remotely to the catheter.

In one embodiment such as in FIG. 1, the signal communicating means 17 has a flexible cable jacket 5 and is connected to a proximal end 13 of the tubing 4 and serves to protect and route the communication means 17 to the processing device 7 after the communication means 17 exits the tubing 4. In this specific case, the communication means 17 runs on the surface of the guiding tube 3, and is secured with an overlay of PET heat shrinkable material, from an exit at the sensor 16 to the entrance or opening 9 into the tubing 4.

Still in reference to the catheter device 80 of FIG. 1, it is understood that the sensor 16 can be any type of sensor small enough to enter into a stenosis region of a vessel, such as fiber optic sensors based on a Fabry-Perot cavity or any other kind of optical sensing mechanism, or piezo-electric sensors. In addition, more than one sensor can be used on a single catheter device. The sensor 16 is adapted to measure a pressure and generate a signal indicative of the pressure which is then sent through the communicating means 17. The signal and the characteristics of the communicating means 17 are thus either electrical or optical in nature depending on the sensor used.

Still in reference to FIG. 1, the processing device 7 comprises in one embodiment a signal conditioning means for formatting the signal received from the sensor to obtain a pressure measurement reading adapted to a specific need or given situation useful to a user. In one case, for example, the processing device is implemented to generate a fractional flow reserve (FFR) of a vascular lesion and/or a pressure gradient measurement across a cardiac valve, based on the pressure measurement reading.

Pressure sensors are devices responsive to very small blood pressure changes; they are thus sensitive devices. In order to deliver high fidelity pressure measurements, it is helpful to isolate the sensor device from unwanted parasitic mechanical stresses.

Figure 2:
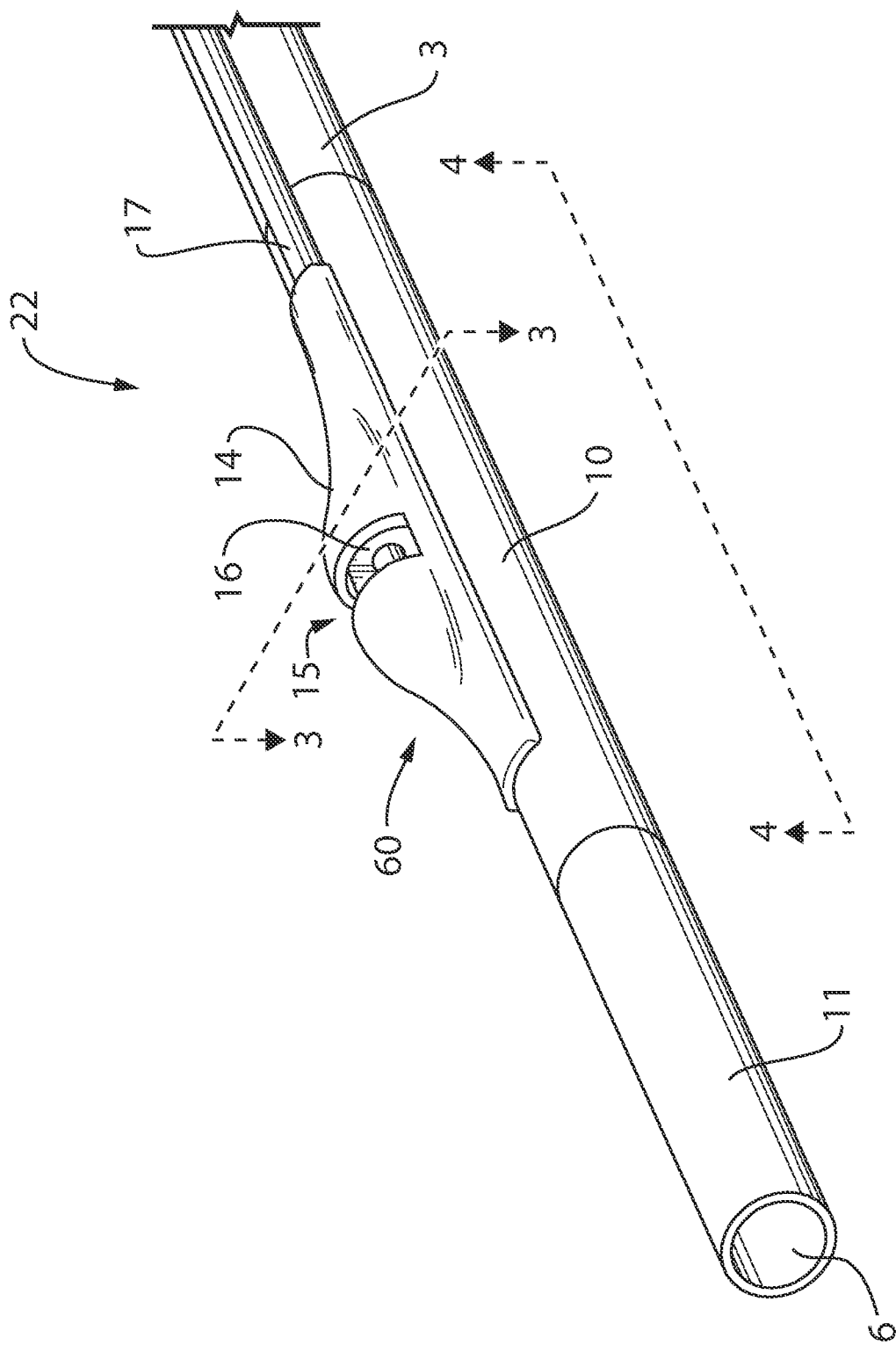
FIG. 2 is a partial perspective schematic view of a distal portion of the catheter device of FIG. 1, in accordance with an embodiment.

In reference to FIG. 2, which shows a portion of distal portion 81 (also referred to as the catheter tip assembly) of the catheter device 80 of FIG. 1, there is also illustrated an example of a protective housing 60 mounted on a wall of the catheter device 80. The housing 60 is designed to have specific characteristics which are dependent on the nature of the sensor 16.

The protective housing 60 shown in FIG. 2 accommodates and protects the tip pressure sensor 16 against undesired mechanical stresses for example. In one embodiment, a thin metal sheet is formed to provide a protective shell 14 to the sensor 16. There is provided in the shell 14 a window 15 (also referred to as an opening) which permits the sensor 16 to sense a pressure in its environment (also referred to as its vicinity).

Once the sensor 16 is well secured in the protective shell 14, the shell 14 with sensor 16, is mounted on a wall of the guiding tube 3. The shell 14 is secured on the wall of guiding tube 3 using an adhesive material such as an epoxy. In one embodiment, it is also covered with an overlay made of a polymer such as polyester (PET) heat shrink having a wall that is as thin as about 0.0005". Alternatively to a thermoplastic or PET heat shrink, any non toxic tubing material which shrinks in size under given conditions is used.

Because catheters need to be pushed in very tortuous vessel paths and against very narrow lesions, it is desirable to further improve the mechanical stability of the sensor. In one embodiment, the shell 14 is mounted on a stiff tube 10 such as a thin wall metal tube of about 0.016" ID. In some instances, the shell 14 is bonded to the stiffer tubing 10 with an epoxy, or welded with a laser or other welding method.

The guiding tube 3 in this example essentially comprises a section of a stiffer tube 10. In some cases, it is desirable to provide the guiding tube 3 by enlarging an inner diameter of the distal end of first tubing 3, fitting and bonding the first tubing 3 over the proximal end of the stiffer tube 10, and fitting and bonding a soft atraumatic section of tubing 11, as best seen in FIG. 2.

Figure 3:
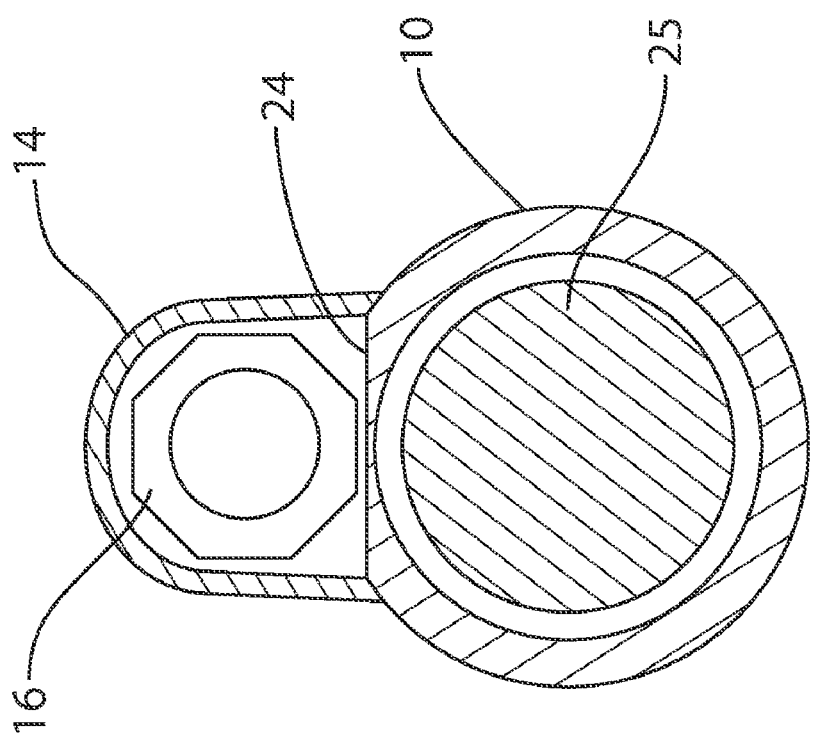
FIG. 3 is a cross sectional view of the distal portion of FIG. 2, taken along line 3-3.

FIG. 3 shows a transversal cross section of catheter tip assembly 22, through the sensor 16, taken along line 3-3 of FIG. 2. It is shown that it is possible to further reduce the size of the catheter tip diameter by machining a flat 24 on the surface of the tube 10, and bringing the sensor 16 closer to the center of the tube on which it sits. The guidewire 25 is shown going through the tube 10.

Figure 4:
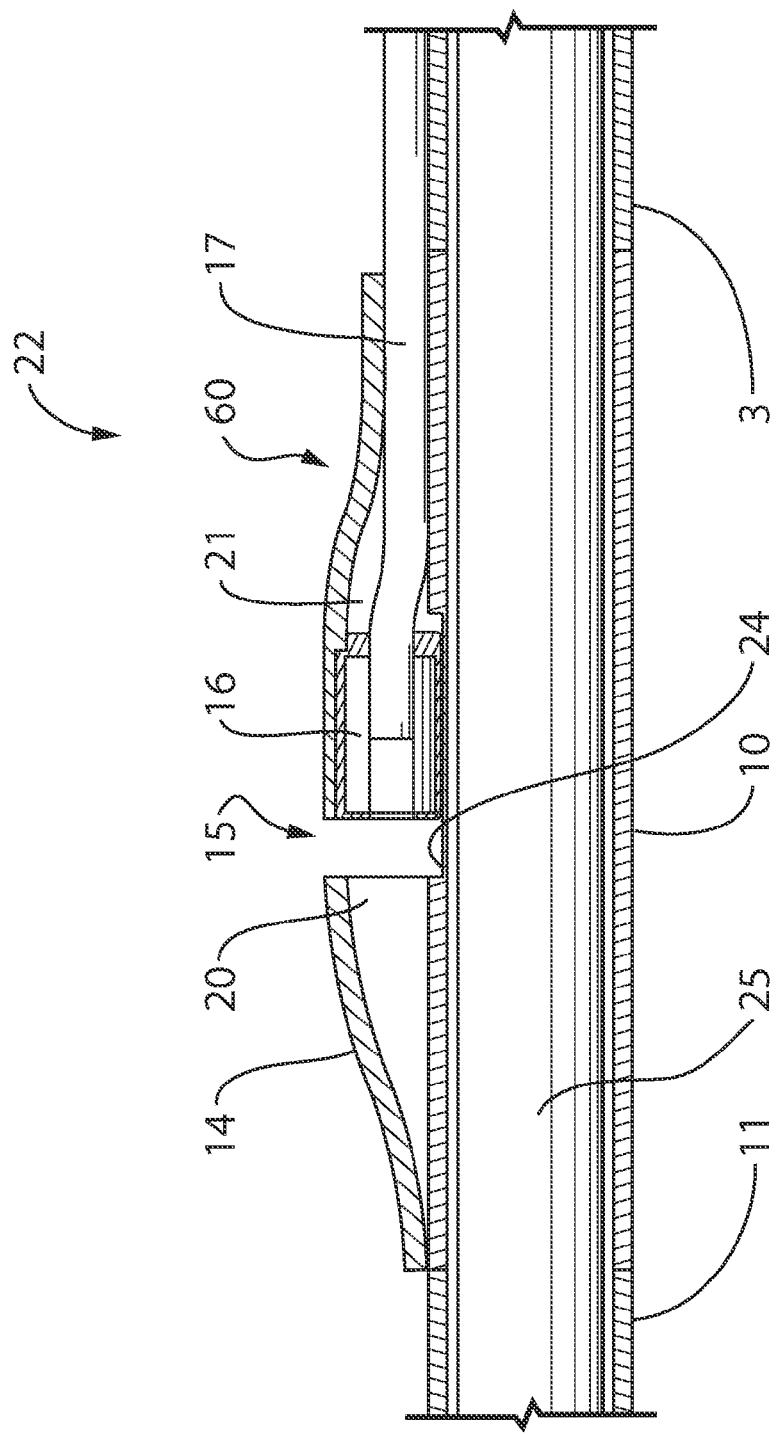
FIG. 4 is a longitudinal cross sectional view of the distal portion of FIG. 2, taken along line 4-4.

FIG. 4 shows a longitudinal cross section of the catheter tip seen in FIG. 2. The sensor 16 is held in place by bonding the communication means 17, such as an optical fiber, near the sensor 16 with an adhesive 21, such as epoxy. The tip pressure sensor 16 may be protected by a thin layer of soft silicone or silicone gel. The volume 20 in the shell 14 opposite to the sensor 16 head can be filled with a polymer to minimize the void under the shell 14, hence minimizing the risk of trapping too large an air bubble. The window 15 adjacent to the sensor 16, at its diaphragm, is left open to permit blood pressure transmission to the tip pressure sensor 16 for pressure sensing. Window 15 can also be filled with silicone gel or silicone oil. If filled with silicone oil, a barrier, such as a thin polymer film or thin layer of silicone, is used to contain the oil in the window 15. Although FIG. 4 shows the guiding tube 3 butted directly against the stiffer tube 10, such a tubing can alternatively be fitted over the stiffer tube 10 to form the guiding tube 3. The same applies for the atraumatic tubing 11.

As previously stated, the guiding tube 3 can be adapted to provide a certain level of pushability and kink resistance suitable to perform as desired. Constraints on kink resistance and pushability may require the use of braided polyimide tubing. For example, with a minimum wall thickness for polyimide braided tubing in the order of 0.0025", the diameter of the guiding tube 3 is set at about 0.021". With these characteristics, the section area of such tubing is thus about 225% the section of a 0.014" guidewire. Such a larger section may cause a pressure drop not related to the stenosis and hence, FFR measurement may differ from one otherwise obtained with a differently sized guidewire such as a 0.014" guidewire mounted with a pressure sensor.

Figure 5:
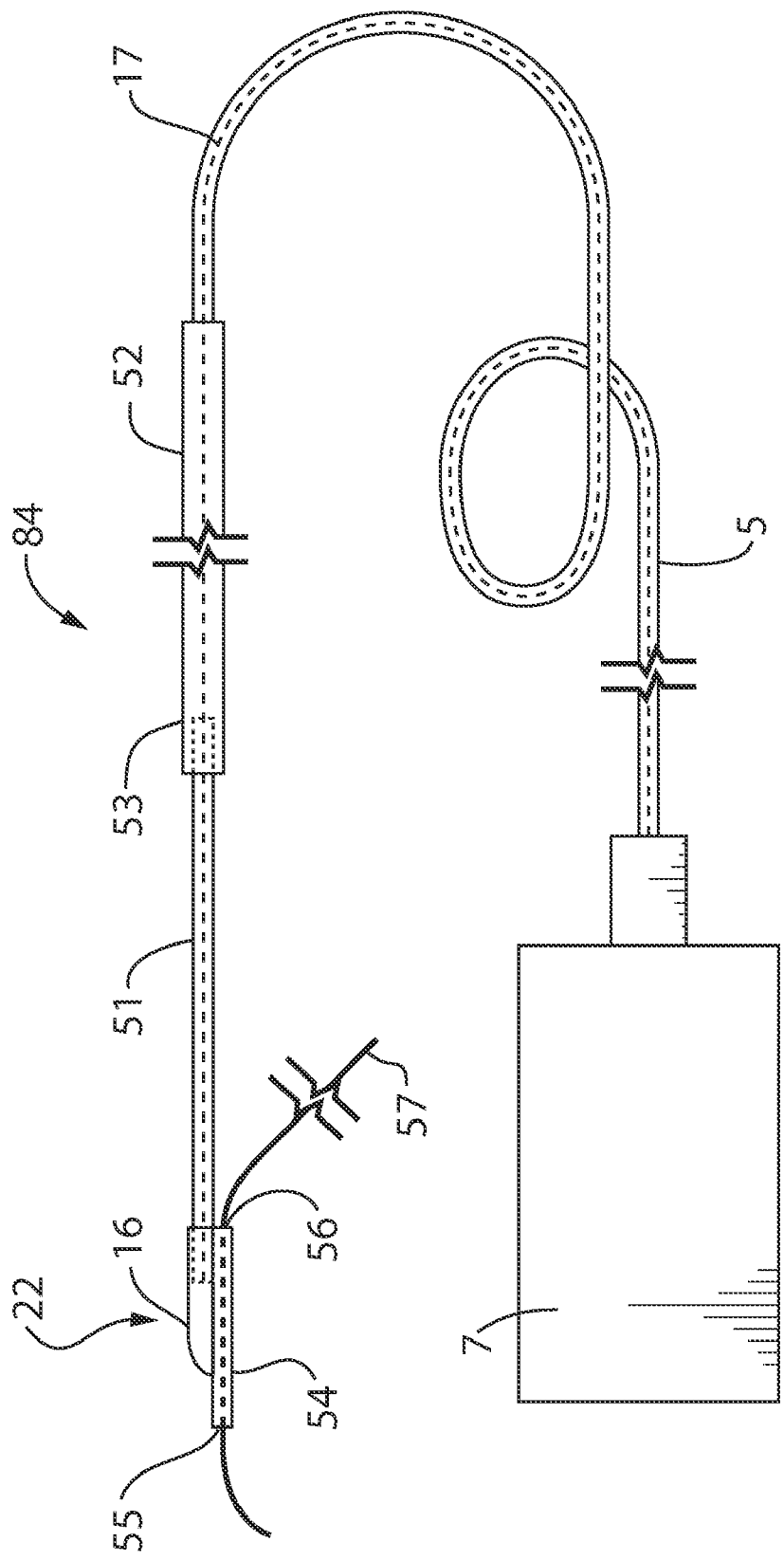
FIG. 5 is a schematic view of a catheter device in accordance with an embodiment where the distal portion has a reduced catheter section.

FIG. 5 illustrates another embodiment for a catheter device 84 similar to the device 80 of FIG. 1, but designed to further minimize the sectional size of the portion of the catheter standing across the stenosis while performing. While performing FFR, the catheter tip 22 is located some 2 to 3 cm distally to the lesion and therefore, hypo-tube 51 is the portion of the catheter standing across the stenosis while performing FFR. This section of the catheter needs to be kept to the smallest possible diameter.

The guiding tube 54 in which the guidewire 57 slides through is significantly reduced in length compared to the embodiment of FIG. 1. The guidewire 57 enters into distal end 55 of the guiding tube 54 and exits from a guiding tube proximal end 56. By way of non limiting example, the length of the guiding tube 54 can be as short as about 1 to 2 cm.

The sensor 16 is eccentrically positioned relative to guiding tube 54. The distal end of first hypo-tube 51 is eccentrically mounted to a wall of the guiding tube 54 and concentrically mounted within sensor housing 60 (see FIG. 6), using a laser welding or other available welding methods. For example, the first hypo-tube 51 has an outside diameter of about 0.009" and an inner diameter of about 0.005". The total obstructive section area of both guidewire and pressure catheter across lesion under scrutiny is given by the addition of 0.014" guidewire 57 and 0.009" hypo-tube 51, both running in parallel. The section area is thus kept to no more than approximately 140% the section of the 0.014" guidewire 57 section area alone.

In one embodiment, proximal end 53 of first hypo-tube 51 is connected to the distal end of second hypo-tube 52, by sliding the proximal end 53 of the tubing 51 into the distal end of the second tubing 52. This connection is in some cases secured by laser welding, friction welding and/or bonding with adhesive. By way of non limiting example, the length of the first hypo-tube 51 is about 20 to 30 cm long. The communication means 17 that connects the sensor 16 to the signal conditioner 7 is guided through both first hypo-tube 51 and second hypo-tube 52. Once exiting the second hypo-tube 52, the communication means 17 goes through a cable jacket 5.

Figure 6:
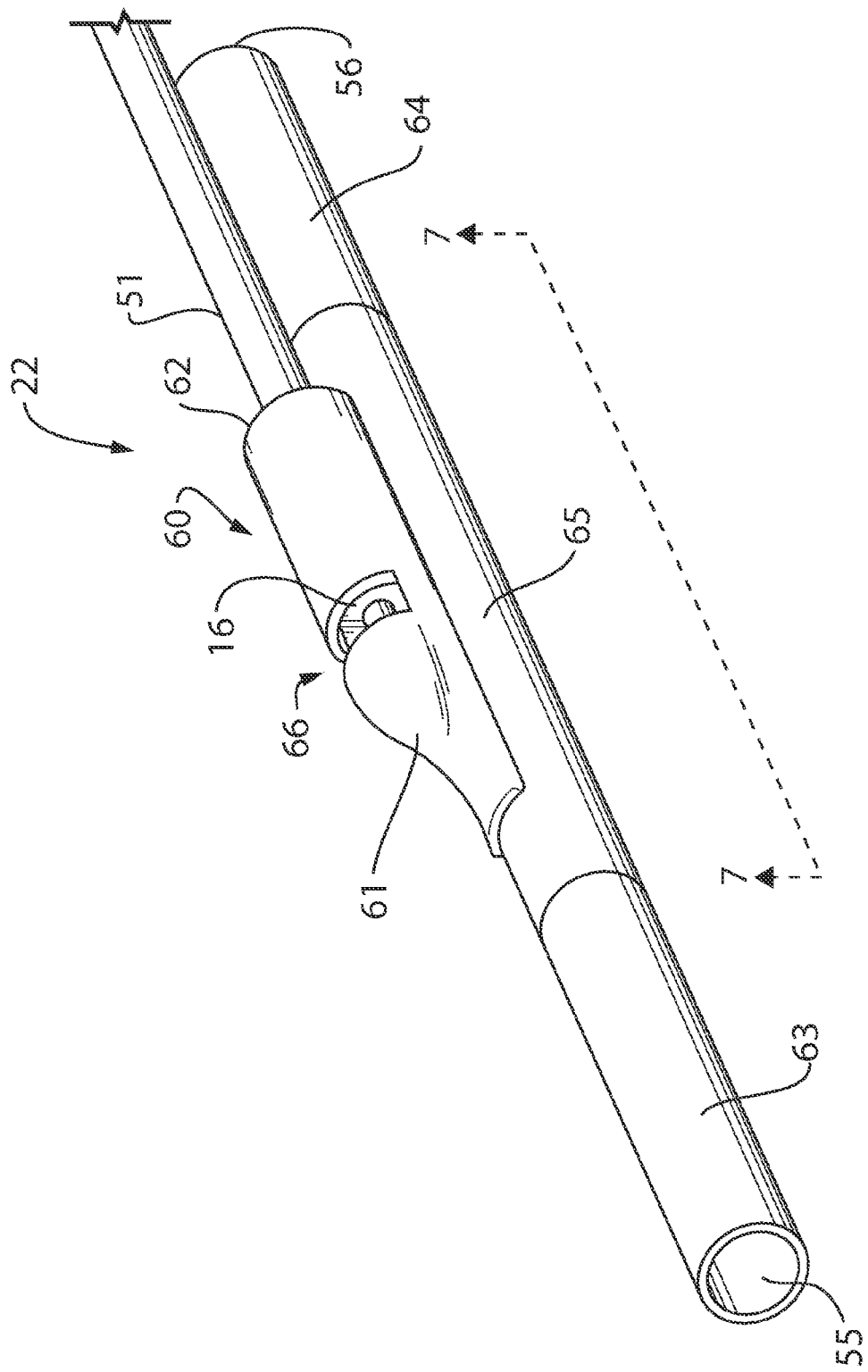
FIG. 6 is a perspective schematic view of the distal portion of FIG. 5, in accordance with a first example.

FIG. 6 shows a schematic of one first embodiment for the distal portion 22 (i.e., the catheter tip assembly) of the catheter device 84 of FIG. 5.

Sensor housing 60 is for the protection of tip pressure sensor 16, such as a fiber optic pressure sensor. In this embodiment, the diameter of sensor housing 60 is of about 0.012" or less. The distal end 61 of the housing (also referred to as a protective shell) 60 protecting the sensor 16 has a form that makes the sensor housing 60 smooth for the wall of blood vessel. The proximal end 62 of the housing 60 has a circular shape to accommodate the first hypo-tube 51. First hypo-tube 51 can be bonded or welded to one or both the housing 60 and metal tube 65. A window 66 is also provided to let the blood pressure transmission to the sensor 16 or permit the sensor to sense the blood pressure from the blood entering the window 66. Both ends of metal tube 65 are connected to soft atraumatic tubings 63 and 64.

Figure 7:
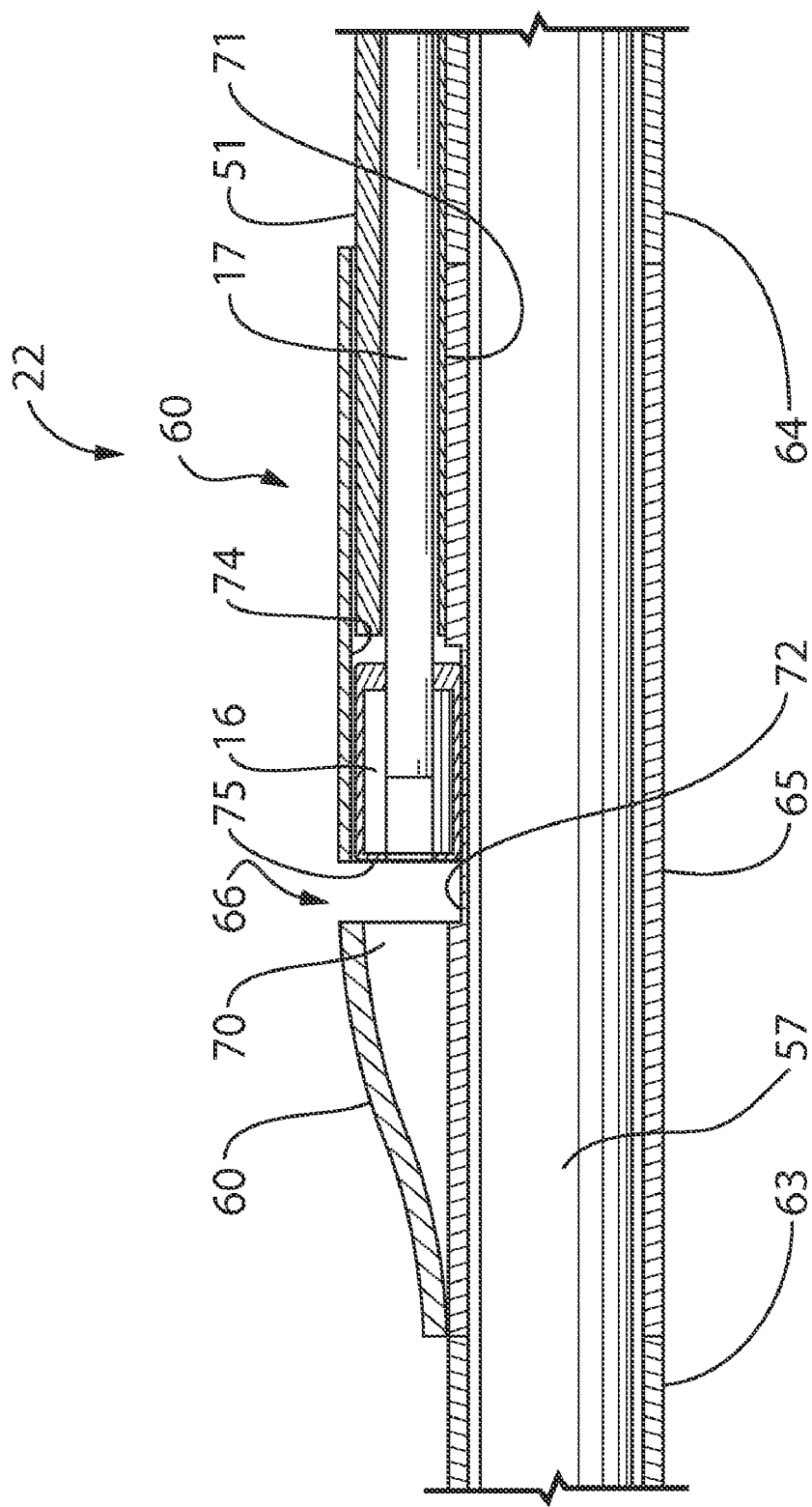
FIG. 7 is a longitudinal cross sectional view of the distal portion of FIG. 6, taken along lines 7-7.

FIG. 7 shows a longitudinal cross section of the catheter tip assembly 58 as shown in FIG. 6. In this embodiment, the communication means 17, here an optical fiber goes through the first hypo-tube 51. To keep the section of the tip of the catheter device 84 at the location of the sensor 16 as small as possible, the metal tube 65 has a flat surface 72. First hypo-tube 51 also has a flattened surface 71 to bring the sensor 16 down within flat surface 72 provided on the metal tube 65.

Still referring to the catheter tip assembly 22 as illustrated in FIG. 7, it is noted that a longer flat surface 72 can alternatively be provided on the metal tube 65 so as to avoid having a flattened surface 71 on the first hypo-tube 51. The cross section of the catheter device 84 at the sensor 16 can be further reduced by thinning the housing 60 in the region 74 where tip pressure sensor 16 and first hypo-tube 51 are positioned. As illustrated in FIGS. 1 to 4 in reference to the window 15, the window 66 can be left open, filled with a soft silicone, a silicone gel or silicone oil.

Figure 8:
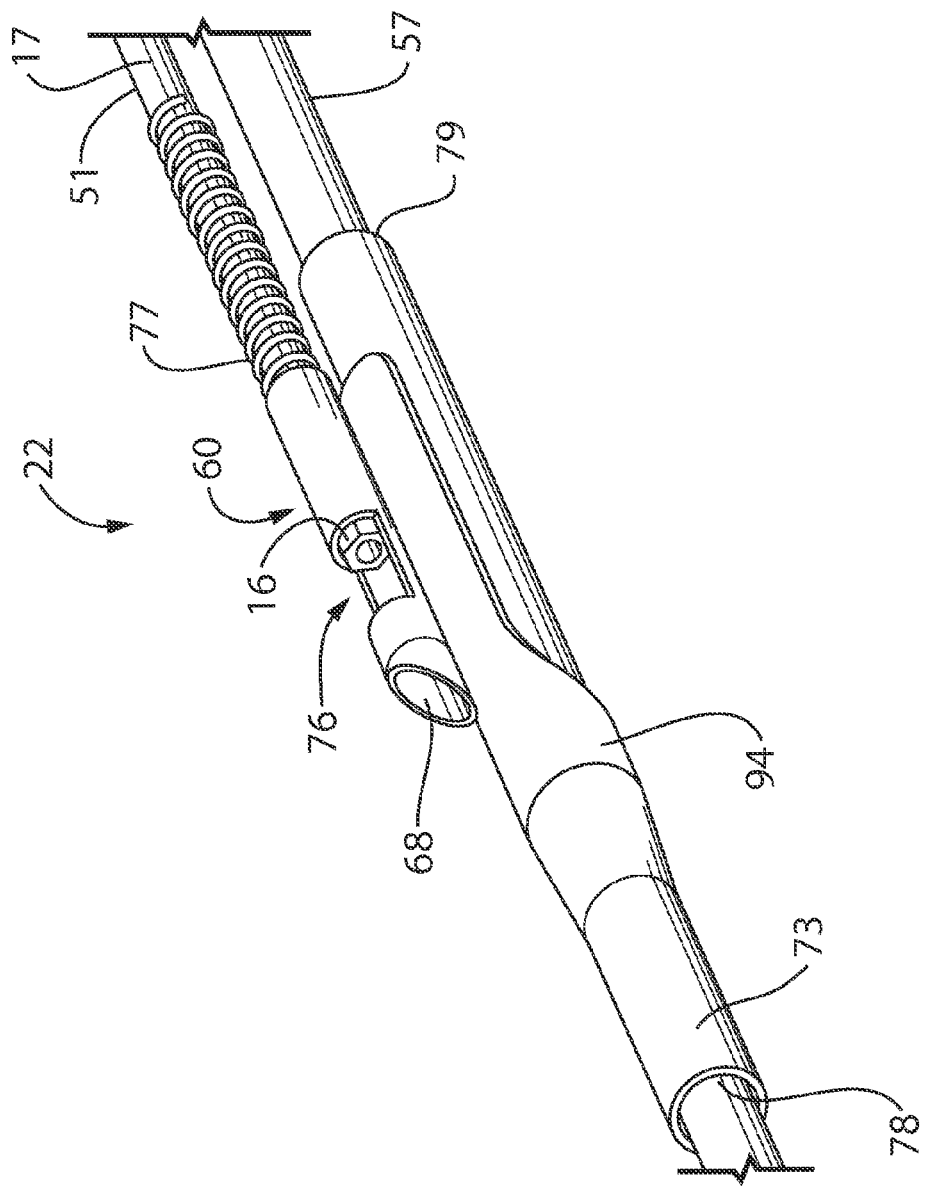
FIG. 8 is a perspective schematic view of the distal portion of FIG. 5, in accordance with a second example.

Relatively long portion of stiff guiding tube 65 (FIG. 6), is compromising good trackability of the catheter over guidewire as it has the effect of forcing the guidewire to locally straighten while tracking over. Also, manufacturability of sensor housing shell illustrated in same FIG. 6 can be improved by replacing with cylindrical tubing. FIG. 8 shows a schematic of such another embodiment for the catheter tip assembly 22 of the catheter device 84.

In this embodiment, the sensor housing 60 comprises a cylindrical tube connected directly to the distal end of the hypo-tube 51. The inner diameter of the sensor housing 60 accommodates the diameter of the sensor 16. By way of non limiting example, the sensor housing 60 has an ID and an OD of the order of respectively 0.010" and 0.012".

The signal communication means 17 for transmitting pressure information from tip pressure sensor 16 travels through the hypo-tube 51 and also the hypo-tube 52 (shown in FIG. 5).

The sensor housing 60 is here provided with one window 76 or multiple windows (not shown) for allowing blood pressure to be transmitted to the tip pressure sensor 16.

In the illustrated embodiment, a short ring-shaped device such as a metal ring 94 is welded to a surface of the sensor housing 60. The metal ring 94 is used to hold in place the guiding tube 73 accommodating the guidewire 57, eccentric with respect to the tip pressure sensor 16, its housing 60 and appended tubing 51. The guidewire 57 enters from guiding tube distal end 78 and exits from guiding tube proximal end 79.

In one embodiment, the guiding tube 73 is made of thin soft material in order to minimize a catheter tip diameter, and to provide atraumaticity. This is advantageous, for example, when the catheter is pulled out of blood vessel without being guided by guidewire.

In the illustrated embodiment, the sensor housing 60 is terminated with a soft atraumatic tip 68. A strain reliever 77 can also be added in some instances to prevent kinking of the hypo-tube 51 connecting to stiffer sensor housing 60.

By way of a non-limiting example, the guiding tube 73 is made of a material such as Teflon™, soft Pebax™ or other similar materials. Similarly, sensor housing 60 and ring 94 are made using for example stainless steel, nitinol, cobalt-chrome material or any other similar materials. Hypo-tube 51 is also preferably made of full hard stainless steel, Nitinol, Cobalt-chromium or other high yield strength materials.

Securing the guiding tube 73 to stiff sensor housing still compromise trackability of the catheter by locally deforming the guidewire while tracking over. Also, securing the guiding tube 73 directly to sensor housing by way of ring 94 results into a non optimal diameter.

Figure 9:
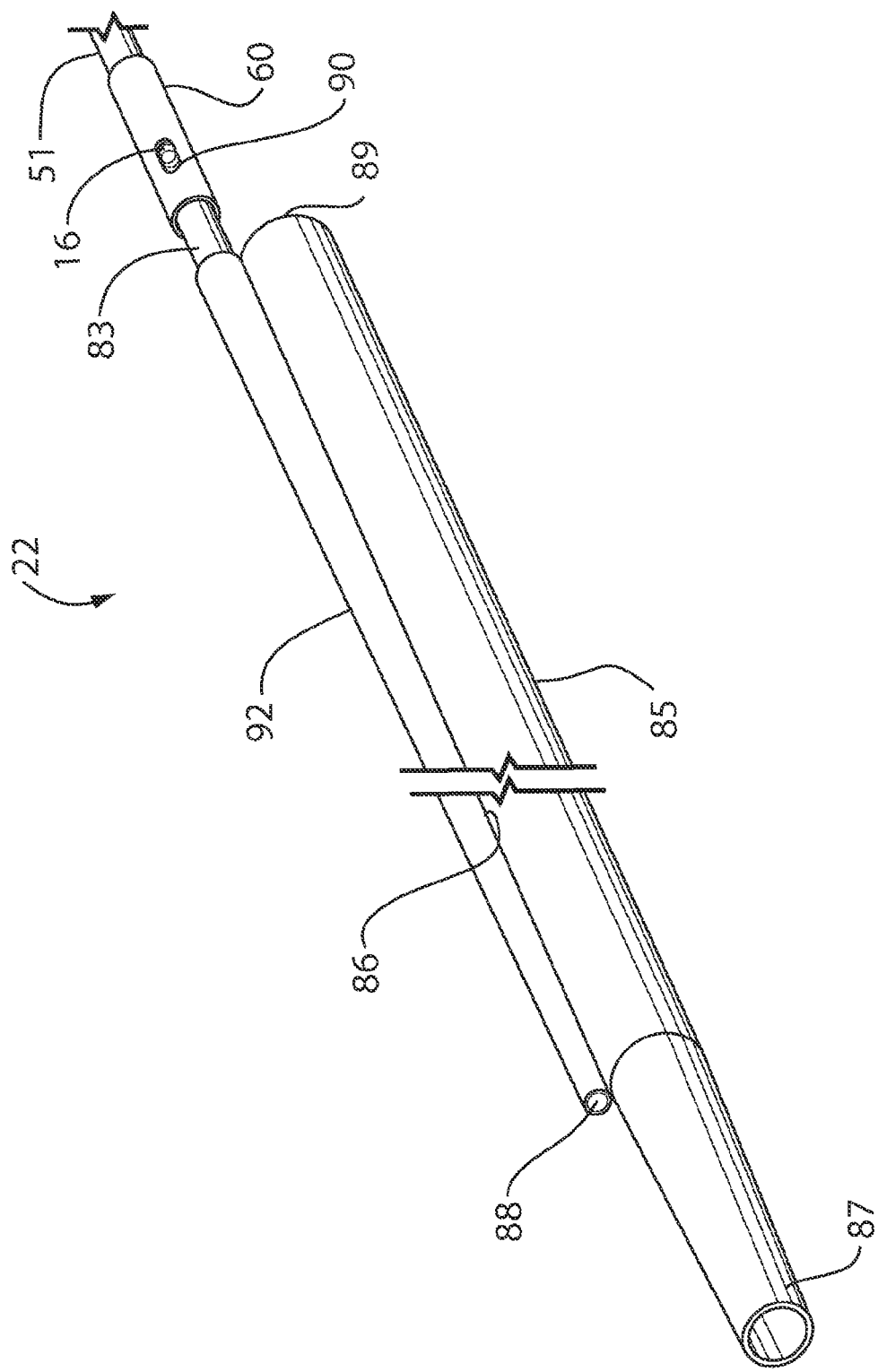
FIG. 9 is a perspective schematic view of distal portion of FIG. 5, in accordance with a third example.

FIG. 9 shows a schematic of yet another embodiment for the catheter tip assembly 22 of catheter device 84. In accordance with one embodiment, this illustrated construction provides a smaller catheter tip diameter compared to the examples illustrated hereinabove, while also providing good flexibility with regard to the optimization of the stiffness of the guiding tube section 85 and therefore, a better trackability.

In the illustrated case, the catheter tip assembly 22 main components include the sensor housing 60, core member 83 connected to sensor housing and extending forward, and guiding tube 85 which again is eccentrically mounted onto a wall of core member 83 and therefore, eccentric to tip pressure sensor 16.

Sensor housing 60 is made out of a cylindrical tube connected directly to the distal end of first hypo-tube 51. The sensor housing 60 is provided with one or multiple windows 90 for allowing blood pressure to be transmitted to the tip pressure sensor 16.

The inner diameter of the sensor housing 60 shall accommodate the diameter of the sensor 16. By way of non limiting example, the sensor housing ID and OD can be respectively of 0.010" and 0.012".

The signal communicating means (not shown) for transmitting pressure information signal from tip pressure sensor 16 travels though first hypo-tube 51 and second hypo-tube 52 (not shown).

In this example, the core member 83 is provided and extends distally to the sensor housing 60. In one embodiment, the core member 83 is tapered in various ways in order to optimize the stiffness of the guiding tube 85 section. In a specific example, core member can be tapered uniformly from 0.008" down to 0.003". The core diameter can also be tapered according to diameter step reduction.

In one example, the core member 83 is made of a hard material with high yield strength for providing desired flexibility such as tempered stainless steel.

Different schemes can be used to attach the guiding tube 85 to the core member 83. One fabrication method consists of shrinking or reflow a polymer tube 92 around core member 83, followed by a reflow process where the guiding tube 85 is fused to the polymer tube 92. In one example, the polymer tube 92 and the guiding tube 85 materials are materials such as Teflon™, Pebax™ and the like. Guiding tube 85 can also include a liner for lowering friction with guidewire (not shown).

In one embodiment, the length of the guiding tube 85 is kept short enough to minimize the overall catheter tip portion 22 extending distally to tip pressure sensor 16. By way of non limiting example, such a length is kept at about 15 mm.

In one embodiment, atraumaticity conditions are kept by having a distal end 87 of the guiding tube 85 extend forwardly relative to a tip 88 of core member 83.

In one embodiment, the distal end 87 of the guiding tube 85 is tapered still to address atraumaticity purposes.

Still referring to FIG. 9, in one embodiment, the tip pressure sensor 16 is provided within the tubing formed by hypo-tube 51, to form a microcatheter. An attachment means such as a short monorail formed by polymer tube 92 is attached to the distal end of core member 83 in order to attach the core member 83 to the guiding tube 85.

The above-described catheter device could easily be extended to other guidewire sizes (i.e. 0.010", 0.014" 0.018", 0.035" and 0.038"). In addition, all of the above mentioned length specifications, tubing characteristics, guidewire sizes, diameters, wall thicknesses and percentages can be varied depending on the specific implementation and desired specifications.

The procedural steps to be taken for measuring a fractional flow reserve (FFR) using the proposed device are described below:

1) The distal end of a guiding catheter is advanced in the aorta and positioned nearby the ostium of the coronary. A fluid filled pressure sensor is connected to the proximal end of the guiding catheter and serves for measuring aortic pressure.

2) A conventional guidewire is then inserted into the guiding catheter and advanced through the stenosis where FFR is to be assessed.

3) The proposed eccentric catheter device is then advanced into the ascending aorta, guided by the guidewire, and positioned near the distal end of the guiding catheter so as to measure the aortic pressure.

4) The pressure taken by the eccentric catheter device's sensor at the distal end thereof, and the pressure taken by the external fluid filled pressure sensor are equalized.

5) The eccentric catheter is then advanced to cross the lesion. In one embodiment, this step involves locating the pressure sensor some 20 mm further than the lesion.

6) The FFR is then obtained by dividing the pressure distal to the lesion which is measured using the eccentric catheter device's sensor, by the aortic pressure measured using the fluid filled pressure sensor connected at the proximal end of the catheter device (i.e. FFR=lesional distal pressure/aortic pressure).

7) The eccentric catheter device is removed.

8) A balloon or stent is then optionally advanced to the lesion, depending on the circumstances specific to a given procedure.

The above method for assessing FFR also optionally involves a step of vasodilating the vessels prior to taking the pressure measurement distal to the lesion (i.e. prior to taking a pressure measurement reading using the sensor on the distal end of the catheter device).

The use of the above-described eccentric catheter device is not limited to coronary applications and can be adapted to perform other pressure gradient or ratio measurements such as but not limited to:

across valves to measure transvalvular pressure gradient,
peripheral (renal, femoral, iliac, tibial) pressure gradient.

In some instances, the catheter device herein proposed is used in the coronary tree to measure coronary FFR. The device can however be adapted to measure pressure gradients or ratio anywhere in the vasculature, such as inside the heart during minimally invasive heart valve surgery, or as a diagnostic tool to measure transvalvular gradient. The catheter may have a single pressure sensor, two or multiple pressure sensors to measure a variety of gradients.

In accordance with one embodiment, the above-described device has a pressure sensor corresponding to a fiber optic sensor which converts a pressure into a spectrally encoded light signal representative of the pressure exerted on the sensor. A variety of other types of pressure sensors can however be used, such as and not limited to, piezoelectric transducers or any other miniature tip pressure sensing devices.

In order to increase sensor fidelity, in one embodiment, the sensing device is packaged on a section of tubing which has an increased stiffness allowing for the support of the sensor at that location.

In accordance with still another embodiment, the length of tubing (hereinabove referred to tubing 3 in FIG. 1, and 54 in FIG. 5) sliding over the guidewire (25 in FIGS. 1 and 57 in FIG. 5) is reduced to provide a diminished section of the overall catheter device in a stenosis area while performing the FFR measurement.

While preferred and exemplary embodiments have been described above and illustrated in the accompanying drawings, it will be evident to those skilled in the art that modifications may be made therein without departing from the essence of the present description. Such modifications are considered as possible variants comprised in the scope of the present invention.

The invention claimed is:

1. A catheter for measuring translesional pressure used in calculating fractional flow reserve (FFR) in a cardiovascular system, the catheter comprising:
a guiding tube adapted for insertion into the cardiovascular system, the guiding tube defining a lumen for sliding a guidewire therethrough, the guiding tube being fully distal to the lesion during measurement of pressure for calculating FFR;
a tip pressure sensor located proximal to the guiding tube for sensing a pressure in the cardiovascular system;
a signal communicating means extending from the tip pressure sensor and for transmitting a signal indicative of the pressure to a processing device in order to obtain a pressure measurement reading and to calculate the fractional flow reserve (FFR) of the lesion based on the pressure measurement reading; and
a miniature hypo-tube for receiving at least a portion of the signal communication means, the miniature hypo-tube standing fully across the lesion during measurement of pressure for calculating FFR, wherein the miniature hypo-tube is made of a high yield strength material comprising one of full hard stainless steel, Nitinol, and Cobalt-chromium.

2. The catheter device of claim 1, wherein the tip pressure sensor forms part of a catheter tip assembly which further comprises a core member on which is mounted the guiding tube.

3. The catheter device of claim 2, wherein the catheter tip assembly further comprises a housing on which is mounted a core member, the housing holding the sensor.

4. The catheter device of claim 3, wherein the housing comprises a window for allowing blood pressure to be transmitted to the sensor.

5. The catheter device of claim 3, wherein the miniature hypo-tube has a diameter smaller than or equal to 0.010" .

6. The catheter device of claim 5, further comprising a larger hypo-tube connecting to the miniature hypo-tube for providing adequate pushability and within which the sensor communication means still goes through.

7. The catheter device of claim 2, wherein the core member diameter is tapered or reduced in step.

8. The catheter device of claim 1, further comprising the processing device to which is transmitted the signal indicative of the pressure.

9. The catheter device of claim 1, wherein the signal communication means comprises one of an optical fiber and an electrical wire.

10. The catheter device of claim 1, wherein the sensor is one of an optical sensor and an electrical sensor.

11. The catheter device of claim 1, wherein the length of the guiding tube is equal or less than 15 mm.

12. A catheter for measuring a pressure in a cardiovascular system, the catheter comprising:
a guiding tube adapted for insertion into the cardiovascular system, the guiding tube defining a lumen for sliding a guidewire therethrough;
a tip pressure sensor proximally mounted relative to the guiding tube, the tip pressure sensor for sensing a pressure in the cardiovascular system; and
a signal communicating means extendinig from the tip pressure sensor and being for transmitting a signal indicative of the pressure to a processing device in order to obtain a pressure measurement reading;
wherein the tip pressure sensor forms part of a catheter tip assembly which further comprises a core member on which is mounted the guiding tube.

13. The catheter device of claim 12, wherein the tip pressure sensor forms part of a catheter tip assembly which further comprises a housing on which is mounted the core member, the housing holding the sensor.

14. The catheter device of claim 13, wherein the housing comprises a window for allowing blood pressure to be transmitted to the sensor.

15. The catheter device of claim 13, further comprising a miniature hypo-tube, wherein the catheter tip assembly connects to the miniature hypo-tube of diameter smaller than or equal to 0.010" and which holds the sensor communication means.

16. The catheter device of claim 15, further comprising a larger hypo-tube connecting to the miniature hypo-tube for providing adequate pushability and within which the sensor communication means still goes through.

17. The catheter device of claim 12, wherein the core member diameter is tapered or reduced in step.

18. The catheter device of claim 12, further comprising the processing device to which is transmitted the signal indicative of the pressure.

19. The catheter device of claim 18, wherein the processing device calculates the fractional flow reserve (FFR) of a vascular lesion based on the pressure measurement reading.

20. The catheter device of claim 19, wherein during the pressure measurement reading, the guiding tube is located distally to the lesion.

21. The catheter device of claim 12, wherein the signal communication means comprises one of an optical fiber and an electrical wire.

22. The catheter device of claim 12, wherein the sensor is one of an optical sensor and an electrical sensor.

23. A catheter for measuring a pressure in a cardiovascular system, the catheter comprising:
- a guiding tube adapted for insertion into the cardiovascular system, the guiding tube defining a lumen for sliding a guidewire therethrough;
- a tip pressure sensor located proximal to the guiding tube, the tip pressure sensor for sensing a pressure distal to a lesion in the cardiovascular system;
- a signal communicating means extending from the tip pressure sensor and being for transmitting a signal indicative of the pressure to a processing device in order to obtain a pressure measurement reading; and
- a miniature hypo-tube for receiving at least a portion of the signal communication means, the miniature hypo-tube having a diameter smaller than or equal to 0.010".

24. The catheter device of claim 23, wherein the tip pressure sensor forms part of a catheter tip assembly which further comprises a core member on which is mounted the guiding tube.

25. The catheter device of claim 24, wherein the catheter tip assembly further comprises a housing on which is mounted the core member, the housing holding the sensor.

26. The catheter device of claim 25, wherein the housing comprises a window for allowing blood pressure to be transmitted to the sensor.

27. The catheter device of claim 26, further comprising a larger hypo-tube connecting to the miniature hypo-tube for providing adequate pushability and within which the sensor communication means still goes through.

28. The catheter device of claim 24, wherein the core member diameter is tapered or reduced in step.

29. The catheter device of claim 23, wherein the signal communication means comprises one of an optical fiber and an electrical wire.

30. The catheter device of claim 23, wherein the sensor is one of an optical sensor and an electrical sensor.

31. The catheter device of claim 23, further comprising the processing device to which is transmitted the signal indicative of the pressure.

32. The catheter device of claim 31, wherein the processing device calculates the fractional flow reserve (FFR) of a vascular lesion based on the pressure measurement reading.

33. The catheter device of claim 32, wherein during the pressure measurement reading, the guiding tube is located distally to the lesion.

* * * * *